United States Patent [19]

Krummel et al.

[11] 4,098,818
[45] Jul. 4, 1978

[54] PROCESS FOR MAKING CARBOXYALKYLATED ALKYL POLYETHER SURFACTANTS WITH NARROW POLYETHOXY CHAIN DISTRIBUTION

[75] Inventors: H. Karl Krummel; Rodney Mahlon Wise, both of Cincinnati, Ohio

[73] Assignee: The Procter & Gamble Company, Cincinnati, Ohio

[21] Appl. No.: 749,503

[22] Filed: Dec. 10, 1976

[51] Int. Cl.$^2$ ............................................. C07C 59/00
[52] U.S. Cl. .............................. 260/535 R; 260/501.1; 260/501.17; 260/535 P; 252/117; 252/170
[58] Field of Search ............... 260/404, 413 S, 413 Q, 260/535 R, 527 R, 535 P; 252/117, 170

[56] References Cited

U.S. PATENT DOCUMENTS

| | | | |
|---|---|---|---|
| 2,183,853 | 12/1939 | Haussmann et al. | 260/404 |
| 2,653,972 | 9/1953 | Ash et al. | 260/531 R |
| 2,677,700 | 5/1954 | Jackson et al. | 260/404 X |
| 3,121,728 | 2/1964 | Bartlett et al. | 260/413 S |
| 3,741,911 | 6/1973 | Shane | 252/527 |
| 3,941,710 | 3/1976 | Gilbert et al. | 252/89 R |

FOREIGN PATENT DOCUMENTS 23,683/75   8/1975   Japan.

Primary Examiner—Winston A. Douglas
Assistant Examiner—John F. Niebling
Attorney, Agent, or Firm—Robert B. Aylor; Richard C. Witte; Thomas H. O'Flaherty

[57] ABSTRACT

Improved process for making carboxyalkylated alkyl polyether surfactants with narrow polyethoxy chain distributions using approximately equimolar ratios of alcohol and alkali metal or alkali metal hydride catalyst. The products are useful in making improved carboxyalkylated alkyl polyether surfactants having specific narrow ranges of ethoxylation and containing less than about 6% fatty alcohol. Detergent compositions containing said alkyl carboxyalkylated polyether surfactants and having less than about 6% fatty alcohol by weight of said alkyl carboxyalkylated polyether surfactants. Processes of making said alkyl carboxyalkylated polyether surfactants.

6 Claims, No Drawings

PROCESS FOR MAKING CARBOXYALKYLATED ALKYL POLYETHER SURFACTANTS WITH NARROW POLYETHOXY CHAIN DISTRIBUTION

BACKGROUND OF THE INVENTION

This invention relates to alkyl carboxyalkylated polyether surfactants of the type disclosed in U.S. Pat. Nos. 2,183,853; 2,653,972; 3,003,954; 3,038,862; 3,741,911; and 3,941,710; British Pat. Nos. 456,517 and 1,169,496; Canadian Pat. No. 912,395; French Pat. Nos. 2,014,084 and 2,042,793; Netherland Patent Application Nos. 7,201,735-Q and 7,406,336; and Japanese Patent Application Nos. 96,579/71 and 99,331/71 (both in the name of Kao Soap Company, Ltd.) all of said patents and said patent applications being incorporated herein by reference.

Such carboxy alkylated alkyl polyether surfactants are typically prepared from alkyl polyether nonionic surfactants having a distribution of analogs of varying oxyethylene chain length including a level of unethoxylated alcohol. It has been discovered that these fatty alcohols are acceptable if they are carboxyalkylated, but are a detriment if they are not reacted. However, it is known that the fatty alcohol is the least reactive species in the normal process of, e.g., carboxymethylation.

It is therefore an object of this invention to provide carboxyalkylated alkyl polyether surfactants having a low level of fatty alcohol.

It is a further object of this invention to provide processes for producing said carboxyalkylated alkyl polyether surfactants having a low level of fatty alcohol.

It is a further object of this invention to provide detergent compositions containing said carboxyalkylated alkyl polyether surfactants and having a low level of fatty alcohol.

It is a further object to provide processes for preparing alkyl polyether precursors which are nonionic surfactants having narrow ranges of ethoxylation and low fatty alcohol contents.

It is a still further object to provide a process for preparing said alkyl polyethers without a solvent.

SUMMARY OF THE INVENTION

In accordance with this invention, a carboxyalkylated alkyl polyether surfactant is provided having the formula

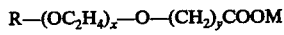

$$R-(OC_2H_4)_x-O-(CH_2)_y COOM$$

wherein R is an alkyl group containing from about 8 to about 18 carbon atoms; $x$ is a number averaging from about 1 to about 12; $y$ is 1 or 2, preferably 1; and M is selected from the group consisting of hydrogen; sodium; potassium; ammonium; mono-, di- and triethanolammonium; mono-, di- and tri-alkylammonium; magnesium and calcium cations and mixtures thereof. Said carboxyalkylated alkyl polyether surfactant comprises at least two homologs having polyoxyethylene chains of different lengths in which each homolog is from about 0% to about 70% by weight of the mixture; said surfactant contains less than about 6%, preferably less than about 4%, of free fatty alcohol; and the distribution of the polyethoxy analogs is such that at least about 40% by weight of the surfactant has polyethoxy chains within ± 1 ethoxy groups of the average ethoxy group content.

DETAILED DESCRIPTION OF THE INVENTION

The carboxyalkylated alkyl polyether surfactants of this invention contain an alkyl chain having from about 8 to about 18 carbon atoms. The alkyl chain can be derived from fatty alcohols, olefins, etc. Normally, and preferably, the alkyl chain will be a mixture of alkyl chains, preferably having a narrow distribution. However, pure alkyl chains can be used. The alkyl chain is desirably a straight saturated alkyl chain, but it may also be a branched and/or unsaturated alkyl chain.

Suitable alcohol precursors of the carboxyalkylated alkyl polyether surfactants of this invention are primary aliphatic alcohols containing from about 8 to about 18 carbon atoms and containing not more than about 70% by weight of the alcohol of 2-alkyl branched material. Other suitable primary aliphatic alcohols are the linear primary alcohols obtained from the hydrogenation of vegetable or animal fatty acids such as coconut, palm kernel, and tallow fatty acids or by ethylene build up reactions and subsequent hydrolysis as in the Ziegler type processes. Preferred alcohols are n-octyl, n-nonyl, n-decyl, u-undecyl, n-dodecyl, n-tridecyl, n-tetradecyl, n-pentadecyl, n-hexadecyl, n-heptadecyl, and n-octadecyl. Other suitable alcohol precursors include primary alcohols having a proportion of branching on the beta or 2-carbon atom wherein the alkyl branch contains from 1 to 4 carbon atoms. In such alcohols at least 30% of the alcohol of each specific chain length is desirably linear and the branching preferably comprises about 50% of methyl groups with smaller amounts of ethyl, propyl and butyl groups. These alcohols are conveniently produced by reaction of linear olefins having from about 11 to about 17 carbon atoms with carbon monoxide and hydrogen. Both linear and branched chain alcohols are formed by these processes and the mixtures can either be used as such or can be separated into individual components and then recombined to give the desired blend.

Typical processes for producing "Oxo" halides which are then used to prepare alcohols are disclosed in U.S. Pat. Nos. 2,564,456 and 2,587,858 and the direct hydroformylation of olefins to give alcohols is disclosed in U.S. Pat. Nos. 2,504,682 and 1,581,988. All of these patents are specifically incorporated herein by reference.

The equivalent secondary alcohols can also be used. It will be apparent that using a single chain length olefin as starting material, a corresponding single chain length alcohol will result, but it is generally more economic to utilize mixtures of olefins having a spread of carbon chain length around the desired mean. This will, of course, provide a mixture of alcohols having the same distribution of chain lengths around the mean.

Primary aliphatic alcohols derived from vegetable oils and fats and from other petroleum feed stocks having alkyl or alkylene groups as part of their structure will also contain a range of chain lengths. Since the range of chain lengths is $C_8$–$C_{20}$ and beyond, it is therefore normal practice to separate the product from such feed stocks into different chain length ranges which are chosen with reference to their ultimate use.

As mentioned previously, commercially available alcohol precursors normally comprise mixtures of alcohols while materials suitable for the purposes of the present invention desirably have a relatively narrow distribution of chain lengths.

The polyoxyethylene portion of the surfactant desirably contains a relatively narrow distribution of the homologous chain lengths. "Narrow distribution" means that at least 40% by weight of the surfactant, preferably 55% or greater, contains polyethoxy groups which are within about one ethoxy group of the average. A more preferred distribution for $C_{12-14}$ alcohols is 55% within one ethoxy group and for $C_{16-18}$ alcohols, 45%. However, it is highly desirable that no more than 70% of the polyoxyethylene groups have the same length since to provide very pure materials for detergent compositions is economically unfeasible. Narrow distributions can be obtained by using acid catalyzed ethoxylation processes and by distillation or steam stripping of the fatty alcohol polyethoxylate prior to, or following, carboxyalkylation. However, acid catalysis gives rise to undesirable by-products such as low molecular weight polyethylene glycols, olefins, decomposition products, etc. and the preferred method for preparation is the one described hereinafter.

The preferred process of preparing the preferred alcohol polyethoxylates having narrow distributions of polyethoxylate chain lengths involves utilizing an essentially 1:1 molar ratio of alkali metal or alkali metal hydride catalyst and fatty alcohol in the ethoxylation step. Suitable alkaline catalysts include sodium and potassium hydrides and the sodium and potassium metals themselves. The ratio of the catalyst to the fatty alcohol on a molar basis can be from about 0.9 to about 1.5, preferably from about 1.0 to about 1.2 to avoid or minimize ester formation in the subsequent optional carboxyalkylation step.

A non-reactive solvent may be added to improve the fluidity of the reaction mix and is essential if the catalyst and the alcohol are mixed together for a long time before the addition of the ethylene oxide. This is required because the alkali metal fatty alcohol alkoxides are solids at all conceivable reaction temperatures, e.g., from room temperature to about 200° C, preferably from about 100° C to about 150° C.

In an even more preferred process, the catalyst is added to the fatty alcohol first and before the complete displacement of the hydrogen from the OH group on the alcohol can occur and while the mixture is still fluid, ethylene oxide is added to start the ethoxylation reaction. This process optimizes the distribution of the ethoxylates while maintaining a fluid reaction mixture without the need for adding a solvent. In effect, the alcohol acts as the solvent for the initial part of the reaction and the alkoxide of the fatty alcohol polyethoxylate is fluid and acts as a solvent for the last part of the reaction. Preferably the ethoxylation reaction is started from about 1 to about 5 minutes after the mixing of the fatty alcohol and the catalyst, and after the alkoxide formation is from about 0% to about 75% complete.

The product of the above reaction has a distribution of polyethoxy homologs in which there is from about 0 to about 70% of each of the homologs and has a "narrow distribution" as defined hereinbefore. These alkali metal alkyl polyethoxides can be reacted with an acid to generate highly desirable nonionic surfactants. But preferably the alkyl polyethoxides are reacted with e.g., alkali metal salts of chloroacetic acid or bromoacetic acid or the corresponding alkali metal salts of chloro- and bromo-propionic acids to generate the desirable carboxymethyl and carboxyethyl alkyl polyethoxylates of this invention.

Carboxyalkylation can also be achieved by oxidation of an alkyl polyoxyethylene nonionic surfactant. However, reacting alkali metal salts of chloroacetic or chloropropionic acids with the fatty alcohol polyoxyethylene surfactant in alkaline medium to effect a coupling is preferred for completeness. Preferably, the carboxy alkyl group is a carboxy methyl group. If carboxyalkylation is around 94% complete, there will, of course, be no more than 6% residual alcohol and/or alkyl ethoxylates.

In summary, the desired low level of fatty alcohol and narrow distribution can be achieved either by removal of the fatty alcohol from the fatty alcohol polyoxyethylene nonionic surfactant prior to carboxyalkylation; extraction or distillation of the fatty alcohols etc. after carboxyalkylation; utilizing a fatty alcohol polyoxyethylene nonionic surfactant which does not contain excessive fatty alcohols etc. because of the process by which the nonionic surfactant is prepared; or by carboxyalkylation to a completeness greater than 94%. The resulting alkyl polyether carboxylate surfactants have improved performance with respect to removal of body soil, grease and oil and particulate soil.

Detergent Compositions

The carboxyalkylated alkyl polyether surfactants of this invention can be used to formulate desirable detergent compositions which are neutral or alkaline during use. Such detergent compositions will normally contain from about 2% to about 50% of said carboxyalkylated alkyl polyether surfactants, preferably from about 10% to about 40% and most preferably from about 15% to about 30%. Since the carboxyalkylated alkyl polyether surfactants of this invention are deliberately prepared so as to contain low levels of fatty alcohol, it is, of course, required that the detergent compositions also contain a very low level of fatty alcohols so as to meet the limits set forth with respect to the carboxyalkylated alkyl polyether surfactant. The detergent composition of this invention can also contain additional surfactants, detergency builders, and minor ingredients as follows.

Surfactants

Optional surfactants include additional anionic surfactants of conventional types, nonionic surfactants, zwitterionic surfactants, ampholytic surfactants, and cationic surfactants. These optional surfactants are typically present at a level from 0% to about 40%, preferably from about 1% to about 20%, and most preferably from about 2% to about 10%. Specific surfactants and mixtures that can be used in the compositions of the present invention are disclosed in U.S. Pat. Nos. 3,664,961; 3,954,632; 3,936,537; 3,932,316; 3,929,678; 3,925,262; 3,915,903; 3,862,058; 3,755,429; and 3,729,431; all of said patents being incorporated herein by reference.

Alkyl ether sulfates of value in compositions of the present invention are disclosed in Belgian Pat. Nos. 807,262 and 807,263 issued on May 13, 1974 and specifically incorporated herein by reference.

Other useful detergent compounds herein include the water-soluble salts of esters of α-sulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety and β-alkyloxy alkane sulfonates containing from about 1 to 3 carbon atoms in the alkyl group and from about 8 to 20 carbon atoms in the alkane moiety.

Alkane sulfonates useful in the present invention are usually mixed secondary alkyl sulfonates having from 10 to 20 carbon atoms in the alkyl chain. Preferably at least 80% and most preferably at least 90% by weight of the alkyl group lies in the $C_{10-17}$ chain length range. Alkane sulfonates are preferably prepared by treating a selected paraffin material of the desired chain length distribution with sulfur dioxide and oxygen to give a secondary sulfonic acid, which is then neutralized with a suitable base. An alternative process utilizes chlorine and sulfur dioxide in the presence of UV light to give sulfuryl chlorides which are then hydrolyzed and neutralized to form the secondary alkyl sulfonates.

Specific preferred detergents for use herein include: sodium linear $C_{10}$–$C_{18}$ alkyl benzene sulfonate; triethanolamine $C_{10}$–$C_{18}$ alkyl benzene sulfonate; sodium tallow alkyl sulfate, sodium coconut alkyl glyceryl ether sulfonate; the sodium salt of a sulfated condensation product of a tallow alcohol with from about 1 to about 3 moles of ethylene oxide; 3-(N,N-dimethyl-N-coconutalkylammonio)-2-hydroxy-propane-1-sulfonate; 3-(N,N-dimethyl-N-coconut-alkylammonio)-propane-1-sulfonate; 6-(N-dodecyl-benzyl-N,N-dimethylammonio) hexanoate; and the water-soluble sodium and potassium salts of higher fatty acids containing 8 to 24 carbon atoms.

It is to be recognized that any of the foregoing detergents can be used separately herein or as mixtures.

Detergency Builders

The detergent compositions of this invention can contain all manner of detergency builders commonly taught for use in detergent compositions. However, because of the superior performance characteristics of the alkyl polyether carboxylate surfactants of this invention, it is possible to formulate detergent compositions which are effective and which do not contain phosphate builders or other sequestering builders. The builders are normally employed in the present compositions at concentrations of from about 0% to about 70%, preferably from about 20% to about 60%, and most preferably from about 30% to about 50%. Useful builders herein include any of the conventional inorganic and organic water soluble builder salts.

Such inorganic detergency builders can be, for example, water-soluble salts of pyrophosphates, orthophosphates, polyphosphates, phosphonates, carbonates, bicarbonates and silicates. Specific examples of inorganic phosphate builders include sodium and potassium tripolyphosphates, pyrophosphates and hexametaphosphates. Detergent compositions incorporating pyrophosphate builders form the subject of the following commonly assigned copending applications and patent that are hereby incorporated by reference, Ser. No. 618,303, Benson, Cherney and Collier, PROCESS FOR PREPARING A PYROPHOSPHATE-SILICATE DETERGENT PRODUCT; filed Sept. 29, 1975 and Ser. No. 713,725, Hau and Cherney, DETERGENT BUILDER AND DETERGENT COMPOSITION, filed Aug. 12, 1976 and U.S. Pat. No. 3,939,100.

The polyphosphonates specifically include, for example, the sodium and potassium salts of ethylene diphosphonic acid, the sodium and potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176; and 3,400,148, incorporated herein by reference.

Non-phosphorus-containing builder salts such as the alkali metal carbonates, bicarbonates and silicates are also useful herein.

Water soluble, organic builders are also useful herein. For example, the alkali metal, ammonium and substituted ammonium polyacetates, carboxylates, polycarboxylates and polyhydroxy-sulfonates are useful builders in the present compositions and processes. Specific examples of the polyacetate and polycarboxylate builder salts include sodium, potassium, lithium, ammonium and substituted ammonium salts of ethylenediaminetetraacetic acid, nitrilotriacetic acid, oxydisuccinic acid, mellitic acid, benzene polycarboxylic acids, and citric acid.

Preferred examples of polycarboxylate builders are set forth in U.S. Pat. No. 3,308,067, Diehl, incorporated herein by reference. Examples of such materials include the water-soluble salts of homo- and co-polymers of aliphatic carboxylic acids such as maleic acid, itaconic acid, measconic acid, fumaric acid, aconitic acid, citraconic acid and methylenemalonic acid.

Additional preferred builders herein include the water-soluble salts, especially the sodium and potassium salts, of carboxymethyloxymalonate, carboxymethyloxysuccinate, cis-cyclohexanehexacarboxylate, cis-cyclopentanetetracarboxylate and phloroglucinol trisulfonate.

A further class of detergency builder materials useful in the present invention are insoluble sodium aluminosilicates, particularly those disclosed in Belgian Pat. No. 814,874 issued Nov. 12, 1974 and incorporated herein by reference. This discloses and claims detergent compositions containing sodium aluminosilicates of the formula

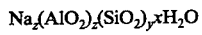

$$Na_z(AlO_2)_z(SiO_2)_y \cdot xH_2O$$

wherein z and y are integers of at least 6, the molar ratio of z to y is in the range from 1.0:1 to about 0.5:1 and x is an integer from about 15 to about 264, said aluminosilicates having a calcium ion exchange capacity of at least 200 mg. eq./gr. and a calcium ion exchange rate of at least about 2 grains/gallon/minute/gram. A preferred material is

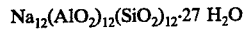

$$Na_{12}(AlO_2)_{12}(SiO_2)_{12} \cdot 27 H_2O$$

Another type of detergency builder material useful in the present compositions and processes comprises a water-soluble material capable of forming a water-insoluble reaction product with water hardness cations in combination with a crystallization seed which is capable of providing growth sites for said reaction product. Builder materials of this type are disclosed in Belgian Pat. No. 798,856 issued Oct. 29, 1973 and incorporated herein by reference.

Minor Ingredients

The compositions herein can optionally contain all manner of additional materials commonly found in laundering and cleaning compositions. Specifically, oxidizing bleaches such as sodium perborate, sodium percarbonate, optionally with bleach precursors such as phthalic anhydride, tetra acetyl ethylene diamine, tetra acetyl methylene diamine or tetra acetyl glycoluril may be incorporated at levels of 1% to 25% of the composition.

Suds suppressors such as blends of silanated silica and silicone fluids, $C_{20-22}$ fatty acids and certain microcrystalline waxes, e.g. Mobilwax 2305 may be employed alone or as mixtures at levels of 0.005% to 5%, preferably 0.01% to 3% and most preferably 0.1% to 1% of the composition.

Viscosity and anticaking aids such as sodium salts of lower alkyl aromatic sulphonic acids are conveniently employed at levels of 0.5% to 5%, particularly if other anionic surfactants are used as part of the surfactant mixture. Other useful anticaking ingredients include the alkali metal salts of sulphosuccinic acid and benzene sulphonic acid.

Certain clays may also be present as emulsification and processing aids in accordance with the teachings in Belgian Patent 821,094, incorporated herein by reference.

Soil suspending agents such as sodium carboxymethyl cellulose and hydroxyethyl cellulose may also be used in amounts of 0.25% to 5% by weight. Other suitable materials useful for this purpose include copolymers of maleic anhydride with ethylene or methyl vinyl ether and certain polymeric glassy metaphosphates.

Enzymes such as the proteolytic enzymes sold under the trade names "Alcalase" and "Esterase" (Novo Industries A/S, Denmark) Maxatase and AZ-Protease (Gist-Brocades NV, The Netherlands) may be incorporated at levels of up to 1% by weight, preferably from 0.25% to 0.75% by weight. Such enzymatic materials may be coated or pilled to aid their stability and to minimize the formation of dust during processing and subsequent storage.

Typical but non-limiting examples of granular compositions in accordance with the present invention comprise by weight of the composition: 2–30%, preferably 10–25% and most preferably 15–20% surfactant; 10–80%, preferably 25–70% by weight of a detergent builder salt; and 1–50% of other optional ingredients such as bleaches, suds suppressors, viscosity and anticaking aids, anti-redeposition agents, fluorescers, enzymes, perfumes, colors, processing aids, corrosion control agents, and antibacterial agents.

Typical but non-limiting liquid detergent compositions embodying the present invention comprise (by weight of the compositions) 5–50%, preferably 20–40% and most preferably 25–35% of an alkyl polyether carboxylate surfactant; in accordance with the present invention and 5–35%, preferably 10–30% and most preferably 10–20% of an additional surfactant which is either another anionic surfactant or a nonionic surfactant. In a preferred embodiment, a source of alkalinity is included at a level sufficient to raise the pH to a value of at least 7.0. For this purpose, free base should be added in excess of that necessary to provide the cation for the anionic surfactant. Any source of free alkalinity can be employed but preferred materials are sodium and potassium hydroxide and alkanolamines. Usage of the latter is normally 1–20%, preferably 2–15%, and most preferably 5–10% by weight of the composition. Optionally builder materials such as pyrophosphates, silicates, and the previously-described synthetic aluminosilicates, citrates, borates, or nitrilotriacetates may be present in solution or dispersed and suspended at levels of 5–20% by weight of the composition. The balance of such compositions normally comprise minor ingredients such as viscosity and gel control agents, perfumes, brighteners, colors, pH control agents and water which conventionally is present at a level of at least 25% by weight.

The following examples illustrate the preparation of the alkyl polyether carboxylate surfactants of this invention and detergent compositions containing said surfactants.

EXAMPLE I

Part A

A sample of carboxymethylated alkyl polyethoxylate surfactant was synthesized by reacting an alkyl polyethoxylate in which the alkyl group contains primarily 12 and 13 carbon atoms and the polyethoxylate portion contains an average of about 3.2 ethoxy groups per molecule with sodium chloroacetate and 50% aqueous sodium hydroxide at 70°–80° C and 5–10 millimeters of mercury pressure. After completion of the reaction, the product was heated to about 150° C and a stream of water was added to the reactor. Heat was maintained until most of the unreacted polyethoxy compound was removed by the stream distillation. This unreacted material was collected and found to contain about 95% unethoxylated fatty alcohols, the remainder being mono- and di-ethoxy alcohols.

Another sample was reacted to the same reaction completeness (i.e., about 88% of the alkyl polyethoxylate are reacted), but was not steam distilled as was the original paste sample.

The above samples were then acidified, separated from the water-soluble salts, and then neutralized to give the following compositions.

| Surfactant Paste Analyses | Steam Distilled A | Not Distilled B |
| --- | --- | --- |
| Anionic in paste | 65.2% | 49.3% |
| Unreacted nonionic | 2.1% | 5.5% |
| By-product Salt | 0.3% | 0.8% |
| Water | 32.4% | 44.4% |
| Fatty alcohol as % of unreacted | 14 % | 70 % |
| Fatty alcohol as % of total active | 0.4% | 7.0% |
| % alkyl polyethoxylate within ± 1 ethoxy group of the average | 43 % | 38 % |

In the above table, sample A is representative of the preferred surfactants of this invention and Sample B is representative of the prior art.

Surfactant A and Surfactant B were tested in a product which was composed of 18% surfactant, 25% hydrated sodium Zeolite A having an average particle size of about 3 microns, 20% of 1.6 ratio of sodium silicate, 24% sodium sulfate, and 10% sodium carbonate.

The two detergent compositions were tested versus a commercial product (Tide containing about 6% phosphorus), the products were tested at a level equivalent to one cup usage for the removal of body soil relative to the reference product. The test involves washing soiled cloth fabrics which are then graded by a panel of experts as to relative cleanness. The body soil removal preformance of the reference product (Tide) was arbitrarily normalized to zero, so the performance of detergent compositions A and B is stated relative to Tide performance. A value of +2.5 units represents a completely clean fabric. The results were as follows:

| Wash Conditions Hardness gr./gal./Temp. (° F) | Composition A | Composition B |
|---|---|---|
| 2/70 | +0.18 | +0.32 |
| 7/70 | +2.20 | +1.29 |
| 9/70 | +1.17 | +0.63 |
| 2/100 | +0.50 | +0.16 |
| 9/100 | +0.82 | +0.40 |

Part B

Two samples of carboxymethylated alkyl polyethoxylate surfactants were prepared. Both were derived from fatty alcohols containing approximately the same alkyl chain lengths and distributions and the polyethoxy portions of the compounds had the same average chain length, but the samples differed in distribution of the various polyethoxy homologs.

The alkyl polyethoxylate feed stock was derived by reacting a $C_{12-13}$ fatty alcohol with approximately three moles of ethylene oxide per mole of alcohol. The alkyl polyethoxylate contained roughly 14% fatty alcohol. This alkyl polyethoxy surfactant was steam stripped until there was only about 1% fatty alcohol present. Both of these materials were carboxylated giving samples as follows:

| | Composition A | Composition B |
|---|---|---|
| Average number carbons in alkyl chain | 12.9 | 12.8 |
| Average number ethoxy groups | 4.5 | 4.7 |
| Portion of alkyl polyethoxylate reacted to give an anionic | 72% | 67% |
| Portion of alkyl polyethoxy material which is unreacted | 28% | 33% |
| Fraction of the alkyl polyethoxylate which is still an alcohol | 7.5% | 1.0% |
| Estimated alcohol in final composition as a percent of the alkyl polyethoxylate feed stock | 5.3% | 0.8% |
| % of alkyl polyethoxylate within ± 1 ethoxy group of the average | 30% | 45% |

The above samples were performance tested in accordance with the procedure set forth hereinbefore using a formula containing 18% surfactant, 18% of the aforementioned zeolite A, 20% 1.6 ratio sodium silicate, 26% sodium sulfate, and 7.7% sodium pyrophosphate. The reference product in this series of tests was a commercial Tide detergent composition containing 0% phosphorus.

Results were as follows:

| Wash Conditions Hardness gr./gal./temp. (° F) | Stripped surfactant body soil removal | Unstripped surfactant body soil removal |
|---|---|---|
| 2/70 | +0.31 | +0.32 |
| 7/70 | +1.31 | +0.91 |
| 9/70 | +1.47 | +0.80 |
| 12/70 | +1.23 | +0.96 |

Part C

One mole of a primary fatty alcohol containing 12 carbon atoms was reacted with one mole of sodium metal at 100° C and diglyme (Bis-2-methoxyethylether) solvent. During the reaction the temperature increased by 15° C and the liquid turned dark although it became lighter thereafter. The formation of the alkoxide turned the mixture opaque. The mixture was then heated up to 150° and 3.5 moles of ethylene oxide per mole of fatty alcohol were added over a period of about 4½ hours. The mixture became clear and light yellow. The reaction was carried out under a flowing nitrogen blanket.

The average molecular weight was about 352 and the ethylene average per mole was about 3.8. The distribution of polyethoxy homologs was as follows:

$E_0$ — 0.7%
$E_1$ — 6.3%
$E_2$ — 17.3%
$E_3$ — 22.4%
$E_4$ — 21.2%
$E_5$ — 15.6%
$E_6$ — 8.6%
$E_7$ — 5.6%
$E_8$ — 2.3%

The alkyl polyethoxylate was carboxymethylated by adding one mole of sodium chloroacetate slurried in diglyme at 80° C. The mixture turned creamy color and the temperature increased approximately 10° C. The reaction continued for about 35 minutes at which point the temperature was 65° C. The heat was then turned on to increase the temperature to 90° C. Agitation was stopped 5 minutes later and the reactor was left overnight under nitrogen. The pH at the end of the reactor was close to neutral. the percentage completeness was about 85.2% leaving about 9.55% of alkyl polyethoxylate surfactant present in the finished reaction mix.

Part D

A primary fatty alcohol containing from 12 to 14 carbon atoms was mixed with sodium metal pellets and before the reaction was complete, when the temperature was about 150° F and prior to solidification, ethylene oxide gas was added in a ratio of about 3 moles of ethylene oxide per mole of alcohol. The reaction continued for about four hours during which time the temperature increased to about 185° F. The resulting material had a molecular weight of about 311 and ethylene oxide content of about 2.54 moles of ethylene oxide per mole of fatty alochol. The polyethylene oxide homolog distribution was as follows:

$E_0$ — 3.8%
$E_1$ — 15.3%
$E_2$ — 25.9%
$E_3$ — 23.8%
$E_4$ — 15.9%
$E_5$ — 10.7%
$E_6$ — 3.5%
$E_7$ — 1.2%

This alkyl polyethoxylate surfactant was carboxymethylated by the addition of 0.05 moles of sodium hydroxide in powder form per mole of fatty alcohol and 1.05 moles of sodium chloroacetate per mole of fatty alcohol. The mixture which was light yellow turned creamy. The temperature of the reaction was originally 60° C and after one-half hour, it increased to 70° C. The reaction mixture was left overnight under a nitrogen blanket and the percentage completeness was 71% and the percent of alkyl polyethoxylate surfactant present was about 20%.

Part E

Samples of the surfactant from the foregoing process were performance tested according to the procedure in Part A using a formula with 18% surfactant, 25% of the zeolite, 20% of 1.6 ratio sodium silicate, 24% sodium sulfate, and 10% sodium carbonate. The results were as follows:

| Wash Conditions Hardness gr./gal./temp. (° F) | Stripped surfactant body soil removal | Unstripped surfactant body soil removal |
|---|---|---|
| 2/70 | +0.78 | +0.45 |
| 7/70 | +0.95 | −0.43 |
| 9/70 | +0.75 | +0.25 |

In the above test the reference product was a commercial detergent, Tide, containing about 6% phosphorus.

EXAMPLE II

Part A

Sodium metal was used as an ethoxylation catalyst in preparing the following polyethoxylated fatty alcohols. The first two runs were with essentially pure dodecanol and the rest were with mixtures of $C_{12}$–$C_{14}$ fatty alcohols. The ratio of ethylene oxide to fatty alcohol is given in column 1; the temperature of the initial ethoxylation reaction in column 2; the time of ethylene oxide addition in column 3; the molar ratio of sodium metal to fatty alcohol in column 4; the percent of fatty alcohol in the product in column 5; and the poisson fatty alcohol content in column 6. Diglyme solvent was added to the first two runs, but no solvent was used for the rest. All reactions were under nitrogen. Runs 12–15 were in an autoclave (12–13 rocking; 14–15 stirred).

| Run No. | EO/OH | Temp. at EO Add. | Time at EO Add. | Na:OH | % OH Unreacted | Poisson % OH |
|---|---|---|---|---|---|---|
| 1 | 3.8 | 150° C | 45 min. | 1.00 | 0.70 | 1.80 |
| 2 | 4.0 | 160° C | 90 min. | 1.00 | 1.02 | 0.95 |
| 3 | 3.9 | 110° C | at 75% Add. of Na (1–2 min) | 1.00 | 0.33 | 1.00 |
| 4 | 3.5 | 120° C | 1–3 min. | 0.75 | 3.89 | 1.60 |
| 5 | 3.5 | 110° C | 1–3 min. | 0.90 | 3.83 | 1.60 |
| 6 | 2.5 | 185° C | 1–3 min. | 1.00 | 3.8 | 5.00 |
| 7 | 4.5 | 190° C | 1–3 min. | 1.00 | 0.19 | 0.50 |
| 8 | 4.1 | 160° C | 15–20 min. | 0.90 | 1.17 | 0.80 |
| 9 | 2.2 | 125° C | 20 min. | 0.50 | 14.63 | 7.50 |
| 10 | 3.5 | 110° C | 23 min. | 0.25 | 8.43 | 1.80 |
| 11 | 1.3 | 110° C | 10–15 min. | 0.05 | 34.84 | 22.50 |
| 12 | 3.2 | 100° C | 35 min. | 1.00 | 3.30 | 2.40 |
| 13 | 2.7 | 75° C | 50 min. | 1.00 | 7.65 | 4.10 |
| 14 | 3.0 | 105° C | 35 min. | 1.00 | 12.28 | 2.80 |
| 15 | 2.8 | 105° C | 1–3 min. | 1.00 | 0.60 | 4.00 |

The higher ratios of ethylene oxide to fatty alcohol will naturally result in lower fatty alcohol contents, regardless of the process. However, there are clear advantages for the higher ratios of catalyst to fatty alcohol and for addition of the ethylene oxide shortly after the addition of the sodium catalyst without a solvent being present.

Similar results are obtained when potassium metal and sodium and lithium hydrides are substituted for the sodium metal and octanol, nonanol, decanol, undecanol, tridecanol, tetradecanol, pentadecanol, hexadecanol, heptadecanol, octadecanol and mixtures thereof are substituted for the alcohols.

Part B

When the above fatty alcohol polyethoxylates from Runs 1–8 are carboxyalkylated as in Example I, superior carboxyalkylated alkyl polyethoxylate surfactants are obtained. When substituted into the detergent compositions of Example I on a part for part basis for the carboxyalkylated alkyl polyethoxylate surfactants, essentially equivalent performance is obtained.

Part C

Samples of the above surfactants 1, 2, 6 and 7 were performance tested according to the procedure in Part E of Example I against the unstripped surfactant. The results were as follows:

| Surfactant | Wash Conditions 70° F Hardness gr./gal. | | | |
|---|---|---|---|---|
| | 2 | 6 | 9 | 12 |
| Run 1 | +0.33 | +1.38 | +1.00 | — |
| Run 2 | −0.15 | +0.55 | +0.44 | +0.61 |
| Run 6 | +0.10 | +0.09 | +0.37 | −0.51 |
| Run 7 | −0.65 | −0.46 | −0.10 | +0.20 |

What is claimed:

1. The process of preparing a carboxyalkylated alkyl polyether surfactant containing an alkyl group containing from about 8 to about 18 carbon atoms and a number of ethoxy groups averaging from about 1 to about 12 and having a narrow distribution of polyethoxylate chain lengths in which at least about 40% by weight of the surfactant has polyethoxy chains within ± 1 ethoxy groups of the average ethoxy group content in which a fatty alcohol containing from about 8 to about 18 carbon atoms is reacted with from about 1 to about 12 moles of ethylene oxide in the presence of an alkali metal or alkali metal hydride catalyst which is present in a molar ratio of catalyst to alcohol of from about 0.9 to about 1.5 and the resulting fatty alcohol polyethoxylate alkoxide is reacted with an alkali metal chloroacetate or chloropropionate in alkaline medium.

2. The process of claim 1 wherein the catalyst is sodium or potassium metal.

3. The process of claim 1 wherein the molar ratio of catalyst to alcohol is from about 1.0 to about 1.2.

4. The process of claim 3 wherein the catalyst is sodium or potassium metal.

5. The process of claim 1 wherein the reaction temperature is from about room temperature to about 200° C.

6. The process of claim 1 wherein the reaction temperature is from about 100° C to about 150° C.

* * * * *